United States Patent [19]

Noguchi et al.

[11] Patent Number: 4,755,357
[45] Date of Patent: Jul. 5, 1988

[54] SAMPLING DEVICE FOR A GAS ANALYZER

[75] Inventors: Naoki Noguchi; Toshikazu Ohnishi, both of Minami, Japan

[73] Assignee: Horiba, Ltd., Kyoto, Japan

[21] Appl. No.: 822,613

[22] Filed: Jan. 27, 1986

[30] Foreign Application Priority Data

Feb. 7, 1985 [JP] Japan .............................. 60-16787[U]

[51] Int. Cl.[4] ...................... G01N 1/22; G01N 21/76; G01N 21/85; G01N 27/62
[52] U.S. Cl. ..................................... 422/103; 422/83; 73/863.71; 73/863.72; 73/863.73; 73/864.83
[58] Field of Search ............... 422/103, 83; 73/864.83, 73/864.84, 863.71, 863.72, 863.73

[56] References Cited

U.S. PATENT DOCUMENTS 4,676,897 6/1987 Kuze et al. ................... 422/70 X

FOREIGN PATENT DOCUMENTS 0116997 9/1979 Japan .

Primary Examiner—Barry S. Richman
Assistant Examiner—Lynn Kummert
Attorney, Agent, or Firm—Wenderoth, Lind & Ponack

[57] ABSTRACT

A sampling device for use with a gas analyzer, has an inlet, a changeover valve connected to the inlet, two branch passages having upstream ends connected in parallel to the changeover valve for having gas to be analyzed directed through one or the other thereof from the inlet depending on the position of the changeover valve, a further changeover valve connected to the downstream ends of the branch passages for opening the downstream ends of the respective ones of the passages when gas to be analyzed is being directed into the respective branch passages, and a capillary for each of the branch passages, each capillary having an upstream end connected to the corresponding branch passage and having the downstream end adapted to be connected to a detector for detecting components of the gas being analyzed.

3 Claims, 1 Drawing Sheet

SAMPLING DEVICE FOR A GAS ANALYZER

BACKGROUND OF THE INVENTION AND PRIOR ART

The present invention relates to a sampling device for gas analyzers using gas detectors such as a FID (Flame Ionization Detector) and a CLD (Chemical Luminescence Detector).

Since a quantity of a sample gas entering a detector such as a FID and a CLD is small, i.e. on the order of several cc/min to several 10 cc/min, the inside diameter of a capillary used in the control of the flow rate must be very small, i.e. from 0.1 to 0.3 mm. This creates a difficulty in that the capillary is inclined to be choked by material included in the sample gas.

There is shown in FIG. 4(A) a known, sampling device in which a sample-supply passage 41 is provided with one capillary 42 connected thereto, and in FIG. 4(B) there is shown a known sampling device in which two capillaries 42 and 42' are connected in parallel and selectively changed over by means of a three-way changeover valve 43.

With the conventional sampling device shown in FIG. 4(A), in the event that the capillary 42 is choked, it must be replaced to continue the measuring operation. It takes much time to replace the capillary, and then it takes several further hours to achieve stabilization of the temperature and return to normal of the level of background noise in the detector output after the replacement of the capillary.

As a result, a great problem has occurred in that if the capillary is choked during the measurement, the measurement can not be resumed for a long time due to the necessity for repair, particularly in an on-line measurement such as the measurement of exhaust gas from a car.

Also, with the conventional sampling device shown in FIG. 4(B), in which the capillaries 42 and 42' are connected in parallel, the passage 45 and the valve 43 used for changing over have too large a volume in comparison with the flow rate of the sample sent to the detector 44 through the capillaries 42 and 42' whereby a dead space is formed, so that there is a defect in that it takes a long time to replace the gas and the response speed of the gas analyzer is greatly reduced.

SUMMARY OF THE INVENTION

The present invention has been made to provide a gas analyzer which overcomes the above-described deficiencies, and seeks to provide a sampling device for an analyzer which is capable of changing over capillaries with minute flow rates without causing a response delay in the detector.

In order to achieve the above-described object, according to the present invention, there are provided a first branch passage and a second branch passage connected to a sample supply passage through a first changeover valve, a second changeover valve connected to a bypass passage being provided at a junction of said two branch passages, capillaries connected to said first branch passage and said second branch passage, respectively, and a detector connected to the downstream end of these capillaries.

A six-way valve combining the functions of two three-way valves substantially joined together, as shown in FIG. 2, can be used for said first changeover valve and said second changeover valve, instead of two three-way changeover valves as shown in FIG. 1. Also, these valves may be operated either manually or automatically.

In addition, in order to use the device with a FID, it is necessary only to connect the downstream end of each capillary to a fuel-supply passage connected to a detector, as shown in FIG. 3. Also, the bypass passage may be provided with a back pressure regulator.

With the above-described construction, in the event that one capillary is choked, the first changeover valve and the second changeover valves are operated, respectively, to stop the inflow of a sample to one capillary and supply the detector with a sample through the other capillary. In addition, since only a required quantity of sample gas is introduced into the capillary from a branched passage and the rest is caused to flow rapidly through the bypass, the time for replacement of the gas after the one capillary is choked can be shortened, whereby the response speed of a detector can be prevented from being reduced.

DESCRIPTION OF THE PREFERRED EMBODIMENTS

Figure 1:
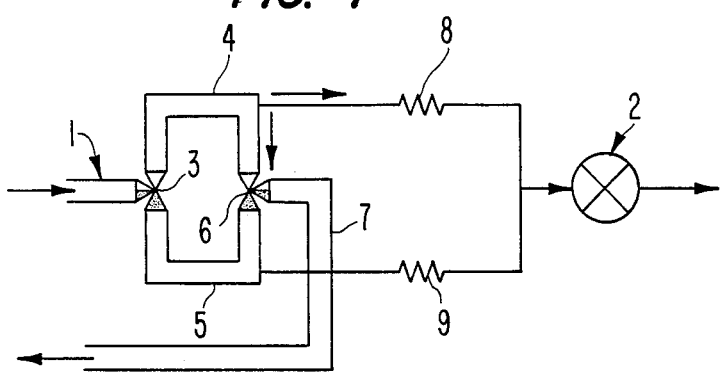
FIG. 1 is a block diagram showing the principal parts of one embodiment of the gas analyzer of the present invention.

Referring now to FIG. 1, a sample-supply passage 1 has the upstream side connected to a sample gas source (not shown). A first changeover valve 3 is connected to the downstream end of said sample-supply passage 1, which valve is here shown as a three-way changeover valve having the inlet connected to the supply passage 1. First and second branch passages 4 and 5 are connected in parallel to each other downstream of said first changeover valve 3, being connected to the two outlets of the changeover valve 3. A second changeover valve 6 has two inlets connected to the downstream ends of said branch passages 4 and 5, which valve is here shown as a three-way changeover valve similar to said first changeover valve 3. A bypass passage 7 is connected to the outlet of the valve 6. Capillaries 8 and 9, hereinafter referred to as a first capillary 8 and a second capillary 9, respectively, have the upstream ends connected to the midpoints of said first branch passage 4 and said second branch passage 5, respectively, and have the downstream ends connected to a conventional gas detector 2, such as the CLD detector referred to hereinbefore.

In the operation of the sampling device constructed as described, when both the first changeover valve 3 and the second changeover valve 6 are open to direct flow through the first branch passage 4 (the condition shown in FIG. 1), a sample sent through the sample-supply passage 1 is sent to the detector 2 through the first capillary 8 and the rest of sample is quickly discharged through the second changeover valve 6 and the bypass passage 7.

With the device in this condition, if said capillary 8 becomes choked, the first changeover valve 3 and the second changeover valve 6 are operated so as to direct the flow through the second branch passage 5, and the sample is supplied to the detector 2 through the second capillary 9. Since, at this time, sample gas remaining within the first changeover valve 3 and the second branch passage 5 is caused to flow quickly into the bypass passage 7 through the second branch passage 5 and the second changeover valve 6 has a small resistance to flow, the detector 2 is supplied with a fresh sample through the second capillary 9 without delay, and also after that the rest of the sample gas flowing through the second branch passage 5 is quickly exhausted through the second changing over valve 6 and the bypass passage 7. The first capillary 8 can then be cleaned, repaired, replaced or the like, while the sample is supplied to the detector through the second capillary.

Figure 2:
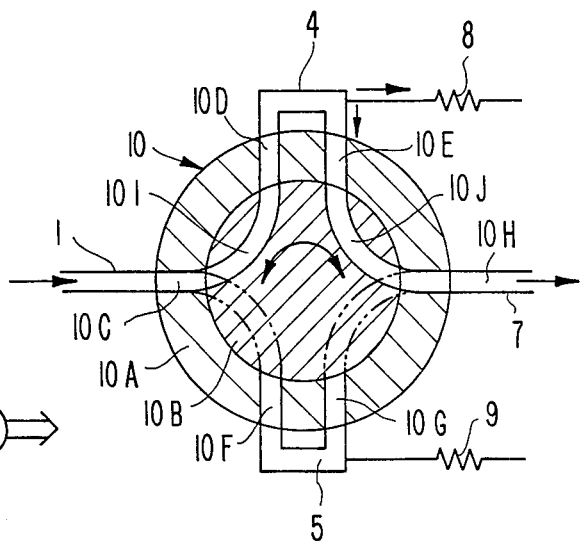
FIG. 2 is a block diagram showing the principle parts of another embodiment of the gas analyzer of the present invention.

FIG. 2 shows another embodiment wherein the functions of two changing over valves 3 and 6 used in the embodiment of FIG. 1 are combined in one valve, that is to say a six-way valve 10. In this embodiment, the following construction is provided.

Valve 10 has a fixed casing 10A, a rotatable valve body 10B rotatable within the fixed casing 10A, an inlet port 10C from the sample-supply passage 1, connecting ports 10D and 10E between which the first branch passage 4 is connected, connecting ports 10F and 10G between which the second branch passage 5 is connected, an outlet port 10H to the bypass passage 7, and connecting passages 10I and 10J formed within said valve body 10B, respectively. The inlet port 10C and connecting port 10D are arranged in a 180°-symmetrical relation to the connecting port 10G and outlet port 10H, the connecting port 10E and outlet port 10H are arranged in a 180°-symmetrical relation to the connecting port 10F and inlet port 10C, and the inlet port 10C is 180° from the outlet port 10H. Accordingly, either the first branch passage 4 or the second branch passage 5 can be connected to the sample-supply passage 1 by rotating the valve body 10B in FIG. 2 by 180°, whereby the detector 2 can be supplied with a sample through either the first capillary 8 or the second capillary 9.

Figure 3:
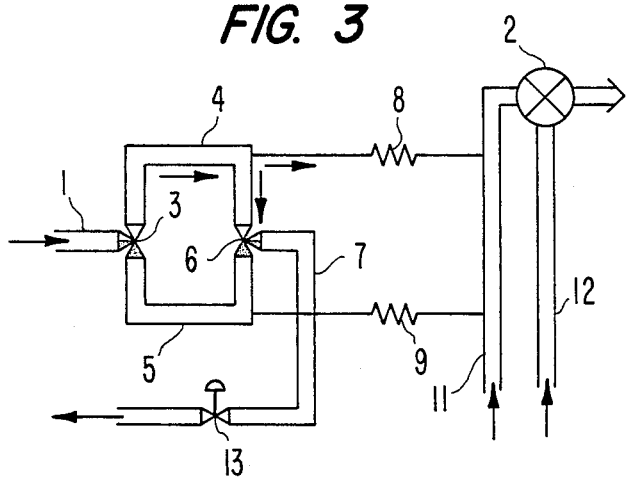
FIG. 3 is a block diagram showing the principal parts of still another embodiment of the gas analyzer of the present invention.

FIG. 3 shows still another embodiment wherein the detector 2 is a FID. A fuel supply pipe 11 extends to the detector 2, and the downstream ends of the first capillary 8 and the second capillary 9 are connected to the fuel supply pipe 11. An air-supply pipe 12 is provided for supplying the detector 2 with combustion air. A back pressure regulator 13 is provided in the bypass passage 7.

As can be understood from the above-detailed description of the embodiments, according to the present invention, in the event that a capillary becomes choked, a changeover valve or valves are changed over to exhaust an accumulation within the device without delay, whereby the measurement can be continued without producing a delay in response at the beginning of the continued measurement. Also, since the rest of a gas introduced into the branch passage is exhausted through the bypass line without delay even when an analyzer is ready for operation, the capillary is in turn supplied with a required quantity of a fresh sample gas in turn, thereby producing no delay in response.

Figure 4A:
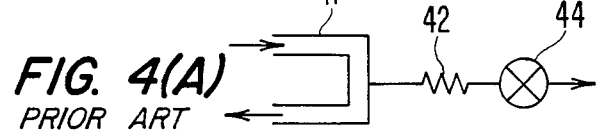
FIGS. 4(A) and 4(B) are diagrams showing the conventional gas analyzers.
Figure 4B:
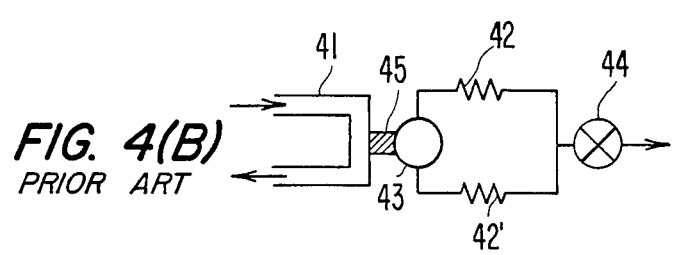

The choked capillary can be replaced or repaired without a useless tie-up of operation of the line and during continued operation of the detector, whereby loss of operating time of the detector can be reduced. Also, the degree of choking in the capillary can be checked by changing over the changeover valves periodically, whereby the time by which the capillary must be repaired or replaced can be estimated. Also, according to the present invention, a dead space and a delay in response of the detector resulting therefrom in the prior art apparatus as shown in FIG. 4(B) are avoided, whereby an accurate measurement can be achieved.

What is claimed is:

1. A sampling device for use with a gas analyzer, comprising:
    an inlet;
    a changeover valve having an air inlet port connected to said inlet and at least a first and a second outlet port, and a valve means movable between a first position in which the inlet port is connected to said first outlet port and a second position in which said inlet port is conencted to said second outlet port;
    at least a first and a second branch passage, each having an upstream end connected in parallel to said first and said second outlet ports, respectively, of said changeover valve for having gas to be analyzed directed through said first or said second branch passage from said inlet depending on whether said valve means is in said first position or said second position, respectively;
    a discharge;
    discharge valve means connected between downstream ends of said first and said second branch passages and said discharge for opening the downstream ends of said first and second passages into said discharge when gas to be analyzed is being directed into the first and second branch passages; and
    a capillary for each of said first and second branch passages, each capillary having an upstream end connected to a corresponding branch passage and having the downstream end adapted to be connected to a detector for detecting components of the gas being analyzed, whereby a desired amount of the gas to be analyzed can be supplied through one or the other capillary and excess gas is discharged into said discharge.

2. A sampling device as claimed in claim 1 in which there are two branch passages, and said changeover valve is a first three-way changeover valve and said discharge valve means is a second three-way changeover valve, the first changeover valve having one port connected to said inlet and the other ports to said first and second branch passages, and the second changeover valve having one port as a discharge port and the other two ports connected to said first and second branch passages.

3. A sampling device as claimed in claim 2 in which said two three-way changeover valves are combined in a six-way changeover valve having a single valve casing in which the ports of the respective changeover valves are located, and having a single valve member movable between a first position in which said first branch passage is open through said ports to said inlet and said discharge and a second position in which said second branch passage is open through said ports to said inlet and said discharge.

* * * * *